(12) United States Patent
Codner et al.

(10) Patent No.: US 9,339,066 B2
(45) Date of Patent: May 17, 2016

(54) PERSONAL COOLING AND HEATING SYSTEM

(71) Applicants: Leon Neil Codner, Fort Worth, TX (US); Jesse DeLance Sutton, Jr., Sanford, FL (US)

(72) Inventors: Leon Neil Codner, Fort Worth, TX (US); Jesse DeLance Sutton, Jr., Sanford, FL (US)

( * ) Notice: Subject to any disclaimer, the term of this patent is extended or adjusted under 35 U.S.C. 154(b) by 0 days.

(21) Appl. No.: 14/845,751

(22) Filed: Sep. 4, 2015

(65) Prior Publication Data

US 2015/0374045 A1 Dec. 31, 2015

Related U.S. Application Data

(60) Provisional application No. 62/076,803, filed on Nov. 7, 2014.

(51) Int. Cl.
| | |
|---|---|
| *A41D 13/002* | (2006.01) |
| *A61F 7/10* | (2006.01) |
| *A61F 7/00* | (2006.01) |
| *A61B 5/024* | (2006.01) |
| *A61B 5/00* | (2006.01) |
| *A61B 5/0205* | (2006.01) |

(52) U.S. Cl.
CPC .............. *A41D 13/0025* (2013.01); *A61F 7/10* (2013.01); *A61B 5/002* (2013.01); *A61B 5/02055* (2013.01); *A61B 5/02438* (2013.01); *A61B 5/6805* (2013.01); *A61F 2007/0018* (2013.01); *A61F 2007/0056* (2013.01); *A61F 2007/0067* (2013.01); *A61F 2007/0096* (2013.01)

(58) Field of Classification Search
CPC ......... A41D 13/015; A41D 1/04; A41D 3/00; A41D 13/0015; A41D 27/28; A41D 13/0025; A62B 17/003
USPC ................. 2/455, 102, 108, 69, 458, DIG. 1; 62/259.3
See application file for complete search history.

(56) References Cited

U.S. PATENT DOCUMENTS

| | | | | |
|---|---|---|---|---|
| 3,713,480 A | * | 1/1973 | Low ................... | A41D 13/0025 165/46 |
| 4,451,934 A | * | 6/1984 | Gioello ............... | A41B 9/00 2/113 |
| 4,575,097 A | | 3/1986 | Brannigan et al. | |
| 4,832,030 A | | 5/1989 | De Canto | |
| 5,515,543 A | * | 5/1996 | Gioello ............... | A41D 27/28 2/69 |
| 5,970,519 A | * | 10/1999 | Weber ................ | A41D 13/0025 2/102 |
| 5,991,921 A | * | 11/1999 | Saito .................. | A41D 13/0025 2/456 |

(Continued)

FOREIGN PATENT DOCUMENTS

| | | |
|---|---|---|
| CA | 2810287 | 9/2014 |
| WO | 2004111741 | 12/2004 |

*Primary Examiner* — Tejash Patel
(74) *Attorney, Agent, or Firm* — Lisa Foundation Patent Law Clinic

(57) ABSTRACT

Embodiments of the invention provide a cooling garment including a garment material configured to be worn on a user's upper body. The garment material includes an outer surface with gel-filled chambers, an inner surface, and a hole therethrough. The garment material is configured to compress against the user's body when worn so that protrusions extending from the inner surface contact the user's body and define air channels between the protrusions, the inner surface, and the user's body. The cooling garment also includes a fixing ring coupled to the garment material around the hole, and a suction device configured to be coupled to the fixing ring, wherein the suction device is configured to circulate air through the air channels.

19 Claims, 9 Drawing Sheets

(56) References Cited

U.S. PATENT DOCUMENTS

| | | | |
|---|---|---|---|
| 6,276,155 B2 * | 8/2001 | Siman-Tov | 165/46 |
| 6,596,019 B2 | 7/2003 | Turner et al. | |
| 6,813,783 B2 * | 11/2004 | Szczesuil | A41D 13/005 |
| | | | 156/290 |
| 7,043,765 B1 | 5/2006 | Ostubo | |
| 7,373,969 B2 | 5/2008 | Chambers | |
| 7,490,606 B2 * | 2/2009 | Duke | A41D 13/0025 |
| | | | 128/201.15 |
| 7,765,616 B2 * | 8/2010 | Gammons | A41D 13/005 |
| | | | 2/115 |
| 8,156,572 B2 | 4/2012 | Whaley | |
| 8,281,609 B1 | 10/2012 | Rothschild et al. | |
| 8,544,115 B1 * | 10/2013 | Gravenstein | A42B 3/285 |
| | | | 2/81 |
| 8,585,746 B2 | 11/2013 | Ilcheva et al. | |
| 8,603,151 B2 | 12/2013 | Latham | |
| 2005/0246826 A1 | 11/2005 | McCarter et al. | |
| 2007/0199124 A1 | 8/2007 | Horn | |
| 2010/0107657 A1 | 5/2010 | Vistakula | |
| 2010/0137953 A1 | 6/2010 | Stein | |
| 2010/0281883 A1 | 11/2010 | Romano | |
| 2011/0302687 A1 | 12/2011 | Whaley | |

* cited by examiner

PERSONAL COOLING AND HEATING SYSTEM

CROSS REFERENCE TO RELATED APPLICATIONS

This application claims the benefit of U.S. Provisional Application No. 62/076,803 filed on Nov. 7, 2014.

BACKGROUND

1. Field of the Invention

The present invention relates to personal cooling and heating systems.

2. Description of Related Art

Heat exhaustion is caused by exposure to high temperatures and is often accompanied by dehydration, for example during outdoor athletic activities. When not treated, heat exhaustion can progress to heat stroke—a medical emergency that can cause damage to the brain and other organs and, in some cases, death. When a person exhibits heat-related symptoms, cooling strategies must be performed as soon as possible to reduce the person's core body temperature. Furthermore, preemptive cooling strategies may be taken to maintain a person's core body temperature within a healthy range to help prevent heat exhaustion. Such preemptive cooling strategies may also boost athletic performance.

One cooling strategy for preventing or treating heat exhaustion includes wearing cooling garments. For example, some cooling vests include pockets for ice packs. A user can remove the ice packs and cool them in a refrigerator or on ice, then re-insert the ice packs into the pockets. These vests tend to be loose and bulky and, as a result, cannot be worn during athletic activities. In addition, because these vests tend to be loose and bulky, they do not conform to the user's body to maximize heat transfer between the user's warm body and the ice packs. In another example, newer cooling vests include sealed compartments with water or gel. These vests are also often made of material that conforms better to the user's body compared to the loose pocket vests. These vests are placed in a refrigerator or on ice to cool the internal water or gel, then worn by the user. Both of the above examples provide passive cooling systems that are no longer useful once the gel or ice returns to room temperature. As a result, during outdoor activities, they are limited to a single, short-term use until they can be placed back on ice or in a refrigerator to be re-cooled.

Active cooling systems, on the other hand, may provide longer cooling benefits compared to passive cooling systems. For example, some active cooling systems require separate cooling mechanisms or components that must be attached to the garment by piping or plugs to cool the garment, either by circulating a cooling fluid through the garment or by cooling electric coils throughout the garment. As a result, these garments are difficult to use during athletic activities, such as running. In addition, active cooling systems require a power supply, such as batteries. Furthermore, many active cooling systems do not maintain cooling effects after the system is shut down. As a result, they must be continually "on" to help cool down the user. Accordingly, these garments may be difficult to use during long-term outdoor activities because the batteries need to be connected to a generator, such as a car battery, for recharging or additional replacement batteries must be carried, adding bulk to the garment.

So as to reduce the complexity and length of the Detailed Specification, and to fully establish the state of the art in certain areas of technology, Applicants herein expressly incorporate by reference all of the following materials identified in each numbered paragraph below.

U.S. Pat. No. 8,585,746 describes a vest with sealed chamber elements filled with liquid, gel, or solid material that can be heated or cooled to moderate an individual's body temperature.

U.S. Pat. No. 7,373,969 describes a personal cooling or warming system requiring a pump to circulate cooling fluid from a separate conditioning unit through the garment.

U.S. Patent Publication No. 2010/0281883 describes a self-contained heating or cooling garment with a fluid pump that circulates fluid throughout the garment. The pump is powered by a battery contained in the pocket of the garment, which may be recharged via a car battery or solar power.

U.S. Patent Publication No. 2010/0107657 describes a vest with heat pipes that plug into a heat capacitor and a separate battery back contained in a pocket of the vest.

U.S. Patent Publication No. 2007/0199124 describes a cooling vest that uses the covering of another jacket and creates a plenum between the wearer's body and the jacket by blowing air into the jacket.

U.S. Pat. No. 8,281,609 describes an air circulation pad, meant to be worn under or between garments, including tubing with holes for delivering air to and exhausting air from the wearer's skin.

U.S. Pat. No. 2005/0246826 describes a cooling garment meant to be worn under a vest, including ribs forming air channels and an air exhaust fan.

Applicants believe that the material incorporated above is "non-essential" in accordance with 37 CFR 1.57, because it is referred to for purposes of indicating the background of the invention or illustrating the state of the art. However, if the Examiner believes that any of the above-incorporated material constitutes "essential material" within the meaning of 37 CFR 1.57(c)(1)-(3), Applicants will amend the specification to expressly recite the essential material that is incorporated by reference as allowed by the applicable rules.

SUMMARY

The present invention provides among other things a cooling garment comprising a garment material configured to be worn on a user's upper body. The garment material includes an outer surface, an inner surface, and a hole therethrough. The outer surface comprises a plurality of chambers filled with gel material, and the garment material is configured to compress against the user's body when worn so that protrusions extending from the inner surface contact the user's body and define air channels between the protrusions, the inner surface, and the user's body. The cooling garment also includes a fixing ring coupled to the garment material around the hole, and a suction device configured to be coupled to the fixing ring, the suction device configured to circulate air through the air channels.

Some embodiments of the invention provide a cooling garment comprising a garment material configured to be worn on a user's upper body and including an outer surface and an inner surface. The cooling garment also includes protrusions extending from the inner surface, and the garment material is configured to compress against the user's body when worn so that the protrusions contact the user's body and define air channels between the protrusions, the inner surface, and the user's body. The cooling garment further includes a suction device coupled to the garment material and configured to circulate air through the air channels. The suction device comprises a piezoelectric power generator configured to generate power to operate the suction device from the user's movements while wearing the cooling garment.

Aspects and applications of the invention presented here are described below in the drawings and detailed description of the invention. Unless specifically noted, it is intended that the words and phrases in the specification and the claims be given their plain, ordinary, and accustomed meaning to those of ordinary skill in the applicable arts. The inventor is fully aware that he can be his own lexicographer if desired. The inventor expressly elects, as his own lexicographers, to use only the plain and ordinary meaning of terms in the specification and claims unless he clearly states otherwise and then further, expressly sets forth the "special" definition of that term and explains how it differs from the plain and ordinary meaning. Absent such clear statements of intent to apply a "special" definition, it is the inventor's intent and desire that the simple, plain and ordinary meaning to the terms be applied to the interpretation of the specification and claims.

The inventors are also aware of the normal precepts of English grammar. Thus, if a noun, term, or phrase is intended to be further characterized, specified, or narrowed in some way, then such noun, term, or phrase will expressly include additional adjectives, descriptive terms, or other modifiers in accordance with the normal precepts of English grammar. Absent the use of such adjectives, descriptive terms, or modifiers, it is the intent that such nouns, terms, or phrases be given their plain, and ordinary English meaning to those skilled in the applicable arts as set forth above.

Further, the inventors are fully informed of the standards and application of the special provisions of pre-AIA 35 U.S.C. §112, ¶6 and post-AIA 35 U.S.C. §112(f). Thus, the use of the words "function," "means" or "step" in the Detailed Description or Description of the Drawings or claims is not intended to somehow indicate a desire to invoke the special provisions of pre-AIA 35 U.S.C. §112, ¶6 or post-AIA 35 U.S.C. §112(f), to define the invention. To the contrary, if the provisions of pre-AIA 35 U.S.C. §112, ¶6 or post-AIA 35 U.S.C. §112(f) are sought to be invoked to define the inventions, the claims will specifically and expressly state the exact phrases "means for" or "step for, and will also recite the word "function" (i.e., will state "means for performing the function of [insert function]"), without also reciting in such phrases any structure, material or act in support of the function. Thus, even when the claims recite a "means for performing the function of . . . " or "step for performing the function of . . . ," if the claims also recite any structure, material or acts in support of that means or step, or that perform the recited function, then it is the clear intention of the inventor not to invoke the provisions of pre-AIA 35 U.S.C. §112, ¶6 or post-AIA 35 U.S.C. §112(f). Moreover, even if the provisions of pre-AIA 35 U.S.C. §112, ¶6 or post-AIA 35 U.S.C. §112(f) are invoked to define the claimed inventions, it is intended that the inventions not be limited only to the specific structure, material or acts that are described in the preferred embodiments, but in addition, include any and all structures, materials or acts that perform the claimed function as described in alternative embodiments or forms of the invention, or that are well known present or later-developed, equivalent structures, material or acts for performing the claimed function.

The foregoing and other aspects, features, and advantages will be apparent to those artisans of ordinary skill in the art from the DETAILED DESCRIPTION and DRAWINGS, and from the CLAIMS.

BRIEF DESCRIPTION OF THE SEVERAL VIEWS OF THE DRAWINGS

A more complete understanding of the present invention may be derived by referring to the detailed description when considered in connection with the following illustrative figures. In the figures, like reference numbers refer to like elements or acts throughout the figures.

Elements and acts in the figures are illustrated for simplicity and have not necessarily been rendered according to any particular sequence or embodiment.

DETAILED DESCRIPTION

In the following description, and for the purposes of explanation, numerous specific details are set forth in order to provide a thorough understanding of the various aspects of the invention. It will be understood, however, by those skilled in the relevant arts, that the present invention may be practiced without these specific details. In other instances, known structures and devices are shown or discussed more generally in order to avoid obscuring the invention. In many cases, a description of the operation is sufficient to enable one to implement the various forms of the invention, particularly when the operation is to be implemented in software. It should be noted that there are many different and alternative configurations, devices and technologies to which the disclosed inventions may be applied. The full scope of the inventions is not limited to the examples that are described below.

Figure 1:
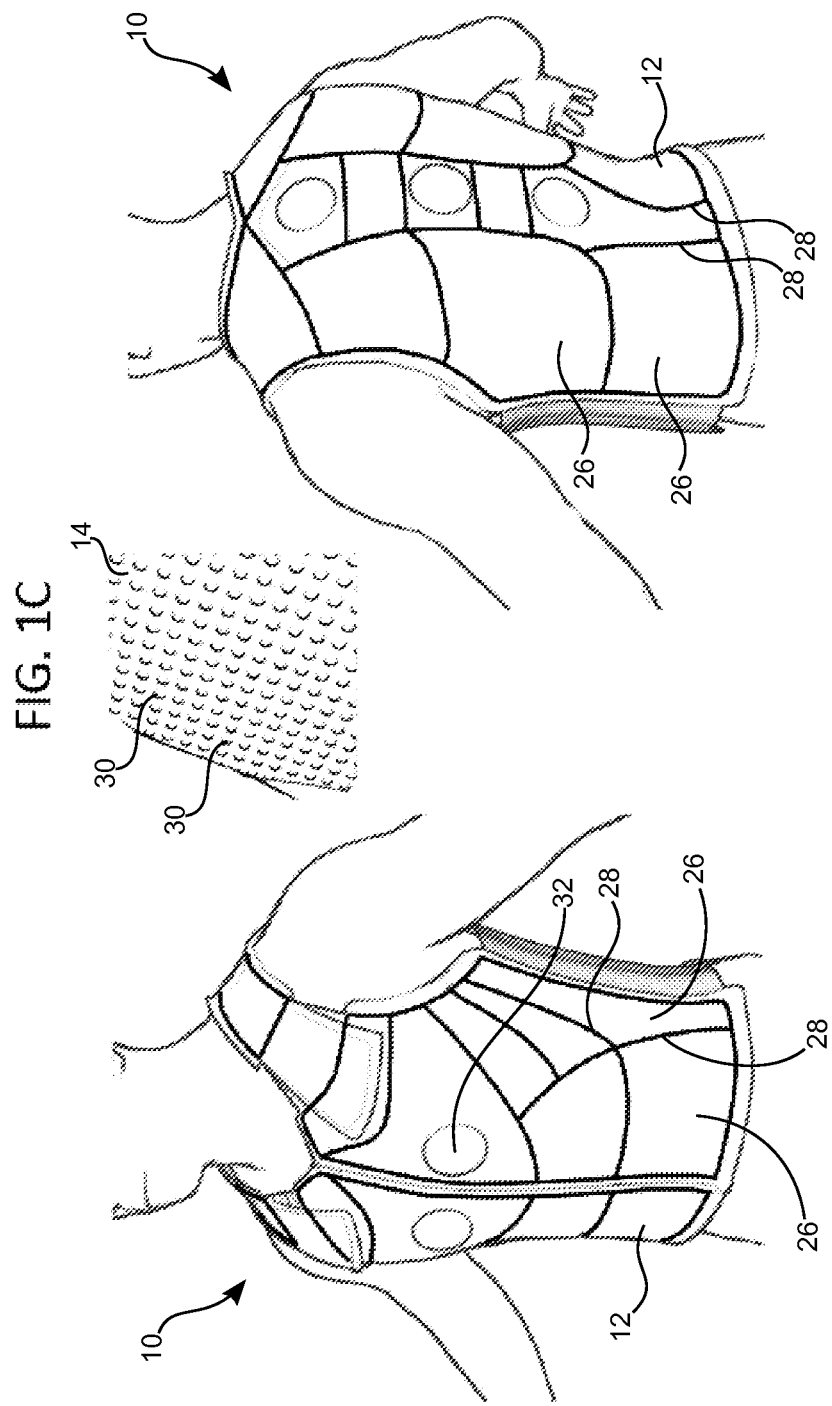
FIG. 1A depicts a front perspective view of a cooling garment according to one embodiment of the invention.
FIG. 1B depicts a rear perspective view of the cooling garment of FIG. 1A.
FIG. 1C depicts a partial interior view of the cooling garment of FIG. 1A.

FIGS. 1A-1C illustrate a cooling garment 10 according to one embodiment of the invention. The garment 10 can include an outer surface 12, as shown in FIGS. 1A and 1B, and an inner surface 14, as shown in FIG. 1C. As shown in FIGS. 1A-3, the garment 10 can also include a zipper 16, tightening straps 18, a neck piece 20, one or more pockets 22, and one or more reflectors 24. As further described below, the garment 10 can be worn by a user to help lower the user's body temperature (e.g., to prevent heat stroke or hyperthermia), to help increase or maintain the user's body temperature (e.g., in cold weather conditions), or for therapeutic uses. The garment 10 may be worn while the user is inactive or resting, or while the user is performing activities, such as running or hiking.

The garment 10 can be a vest or shirt, i.e., configured to be worn on a user's upper body, and can be made of breathable material with stretchable or compression qualities so that the garment substantially contacts the user's body when worn. The compression material of the garment 10 can be substantially light and, as a result, can facilitate comfortable use during activity compared to bulkier, heavier cooling vests. In the vest form, as shown in FIGS. 1A-3, the garment 10 can include the zipper 16 (i.e., a front-close zipper) and the tightening straps 18 to facilitate a tight or compressed fit against the user's body. In one embodiment, the tightening straps 18 can be located around the torso and the shoulder areas of the user and can facilitate tightening the garment 10 against the user's body using Velcro™ attachments or other suitable coupling methods. For example, each tightening strap 18 can include one or more ends directly coupled to the outer surface 12 and one or more detachable ends or flaps equipped with Velcro™. The detachable ends can be pulled across the user's body to a selected tightness, and then reattached to mating Velcro™ on the outer surface 12.

As shown in FIGS. 1A and 1B, the outer surface 12 can include a plurality of compartments 26 filled with a gel material. In some embodiments, the compartments can be completely separate from one another, separated by weld lines 28. As a result, the gel material does not travel between compartments 26. In some embodiments, the weld lines 28 can be strategically positioned along the garment 10 relative to the user's body to facilitate flexibility of the garment 10 as the user moves. Additionally, in some embodiments, while the gel material is completely enclosed within the compartments 26, the gel material may be a nontoxic material to maintain safe use of the garment 10 if one of the compartments 28 is accidentally pierced. The gel material may generally comprise any material that maintains flexibility when frozen, such as material used in gel ice packs or water with dish soap.

The gel material may be cooled or heated in order to cool or heat the garment 10. As a result, the cooled or heated garment 10 can be worn to aid the user during activity or after activity. For example, a user may place the garment 10 in a refrigerator, a freezer, or on ice to cool the gel material. Once cooled, a user may wear the garment 10 to help lower the user's core body temperature. In one embodiment, once cooled, the gel material may maintain its cooled temperature for about 45 minutes when the garment 10 is worn by a user. In some embodiments, the gel chambers 26 can be strategically sized to better cool certain areas of the upper body (such as larger chambers 26 near the user's arm pits) in order to reduce the user's body temperature. Additionally, the gel material may remain flexible when cooled so that the garment 10 contours to the user's body to facilitate maximum contact and heat transfer, unlike bulky ice-pack vests. In another example, the user may wear the garment 10 after activity for therapeutic effect, such as by heating the garment 10 before wearing.

Figure 3:
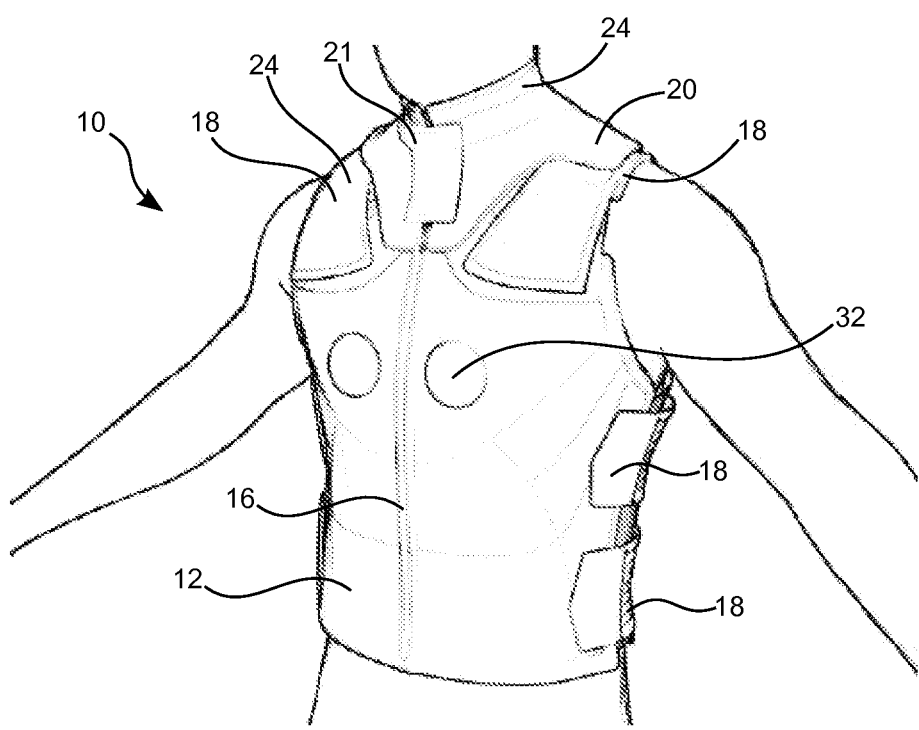
FIG. 3 depicts a front perspective view of a cooling garment according to yet another embodiment of the invention.

In addition, the reflectors 24, as shown in FIG. 3, can facilitate longer cooling action of the garment 10. More specifically, the reflectors 24 can be mirror-type reflectors and can reflect, for example, sunlight off the garment 10 to prevent unwanted heating of the garment 10 and, thus, the gel material while the user is wearing the garment 10. Alternatively, in some embodiments, the garment material can comprise a plastic material manufactured with or sprayed with an ultraviolet (UV) protectant to protect the garment 10 against the sun's rays. For example, the UV protectant can reject (i.e., reflect) heat and UV radiation. The UV protectant can help protect the life and, in some embodiments, color of the plastic material. The plastic material may also allow for easy cleaning of the garment 10, for example, with soap and water.

Furthermore, as shown in FIGS. 1A, 1B, and 3, the neckpiece 10 can wrap around the user's neck and, in some embodiments, upper back and shoulders. The neckpiece 20 can be detachable from the garment 10 and separately cooled or heated. As a result, the neckpiece 10, when pre-cooled, can help lower the user's core body temperature by cooling the neck near the user's pulse point (i.e., near the user's carotid artery). The neckpiece 20 can be secured in place around the user's neck via a Velcro™ attachment 21 (as shown in FIG. 3) or through other suitable coupling methods. Additionally, the neckpiece 20 can include, for example, Velcro™ attachments (not shown) in order to attach the neckpiece 20 to the garment 10. The neckpiece 20 can comprise the same stretchable material as the garment 10 and, in some embodiments, the neckpiece 20 can also include reflectors 24 and/or gel-filled compartments (not shown).

Figure 2:
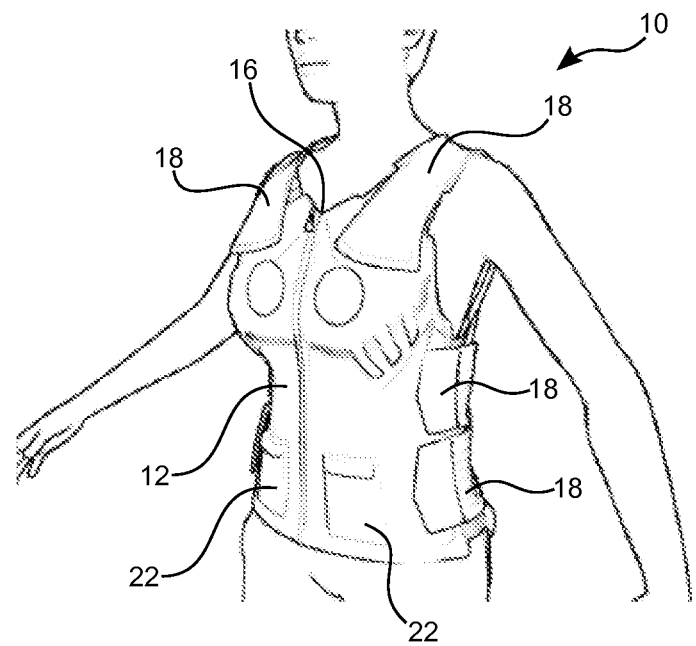
FIG. 2 depicts a front perspective view of a cooling garment according to another embodiment of the invention.

Additionally, in some embodiments, the pockets 22 can be located at a front portion of the garment 10, as shown in FIG. 2, or in another suitable location along the garment 10. The pockets 22 can be used to store items, such as a cell phone, keys, nutrition or energy bars, etc. In some embodiments, the pockets 22 can include a zipper or Velcro™ closure.

Referring now to the inner surface 14, as shown in FIG. 1C, the garment 10 may include protrusions 30 spaced apart and protruding from the inner surface 14. The protrusions 30 can contact the user's body when the user wears the garment 10 to facilitate heat transfer between the user's body and the garment 10. In addition, the protrusions 30 can serve a therapeutic or massaging effect. Additionally, the inner surface 14 may comprise one or more sensors (located along sensor areas 32, as shown in FIG. 1A) to sense or measure one or more user variables, such as heart rate (pulse), temperature, or other variables related to a wearer's cardiac, metabolic, or central nervous system. In one embodiment, the sensor area 32 further includes a wireless or Bluetooth transmitter configured to deliver sensed or measured user variables in real time to, for example, the user's smartphone (e.g., stored in his pocket 22) via a phone application, smartwatch, or any other Bluetooth device. The sensor area 32 may be positioned for proper measurements, such as near the user's heart, under the user's sternum, or along the neckpiece 20 near the user's carotid artery.

Figure 4:
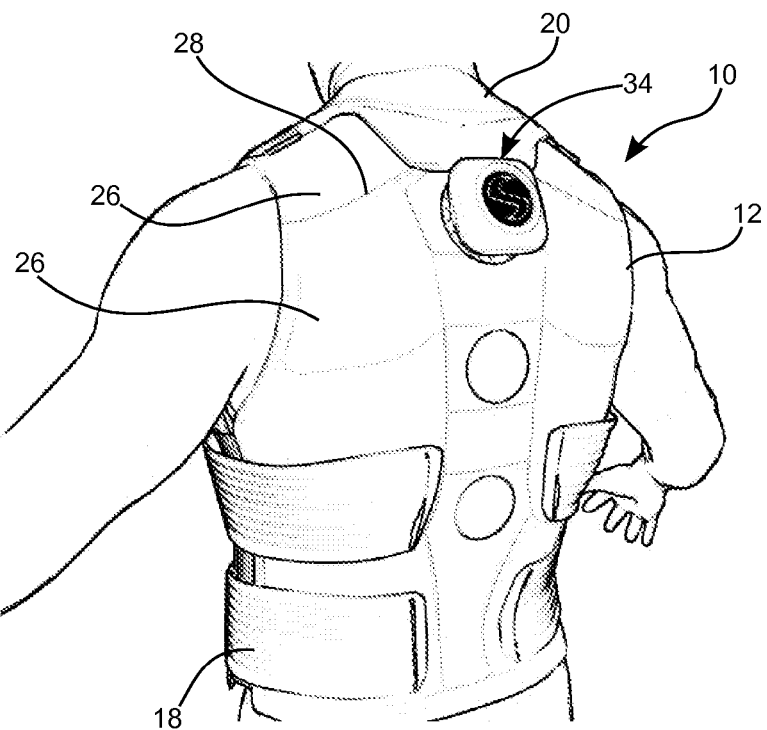
FIG. 4 depicts a rear perspective view of a cooling garment according to yet another embodiment of the invention.

FIGS. 4-13 illustrate the garment 10 according to other embodiments of the invention. The garment 10 can include an outer surface 12, an inner surface 14, a zipper 16, tightening straps 18, a neck piece 20, a pocket (not shown), reflectors 24, and gel-filled compartments 26. These elements may be similar to those described above with respect to FIGS. 1-3. In addition, as shown in FIG. 4, the garment 10 can include a suction device 34 that extends through the garment material from the outer surface 12 to the inner surface 14, as further described below. The suction device 34 can be substantially compact and strategically placed, for example along the user's upper back, to prevent bulk, bouncing, and uncomfortable use of the garment 10 during activities, such as running or hiking.

Figure 5A:
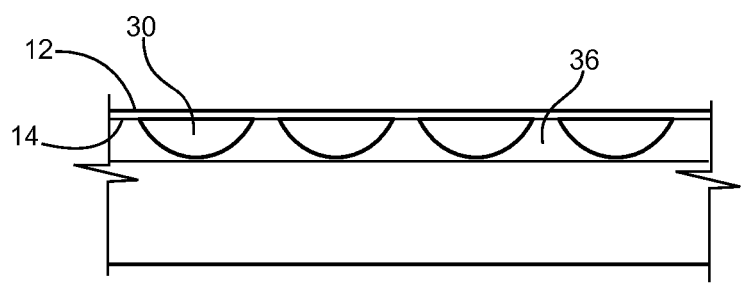
FIG. 5A depicts a cross-sectional view of a cooling garment according to one embodiment of the invention.
Figure 5B:
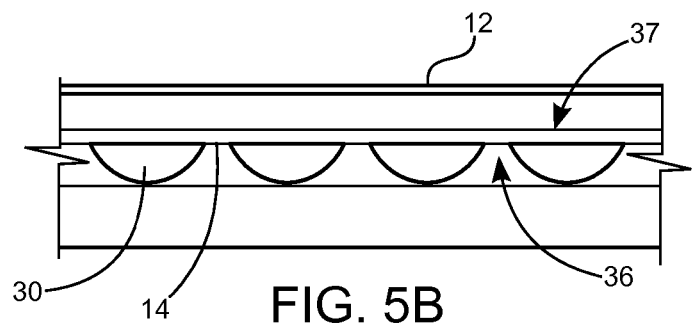
FIG. 5B depicts a cross-sectional view of a cooling garment according to another embodiment of the invention.

The suction device 34 can be configured to circulate air between the garment 10 and the user's body. More specifically, as shown in FIGS. 5A-5B, the protrusions 30 on the inner surface 14, when worn, define air channels 36 between the protrusions 30, the inner surface 14, and the user's body. The suction device 34 can circulate air through the air channels 36 by forcing air from the air channels 36, through the suction device 34, and outward away from the garment 10. As a result, the suction device 34 can increase evaporation of the user's sweat by circulating air through the air channels 36 and then releasing the moist air outside the garment 10, thus providing an evaporative cooling effect. The suction device 34 therefore extracts air and moisture via the air channels 36. Furthermore, the suction device 34, by circulating air between the garment 10 and the user's body, can help maintain the gel material at a cooler temperature for a longer period of time, compared to the garment 10 of FIGS. 1-3, thus lengthening the useful wear time of the garment 10. Additionally, in some embodiments, as shown in FIG. 5B, the garment 10 can include an internal air insulation layer 37 to further facilitate cooling of the user. In such embodiments, the air insulation layer 37 can be located outward from the gel-filled compartments 26 (i.e., the gel-filled compartments 26 are located between the air insulation layer 37 and the wearer's body.

Figure 6A:
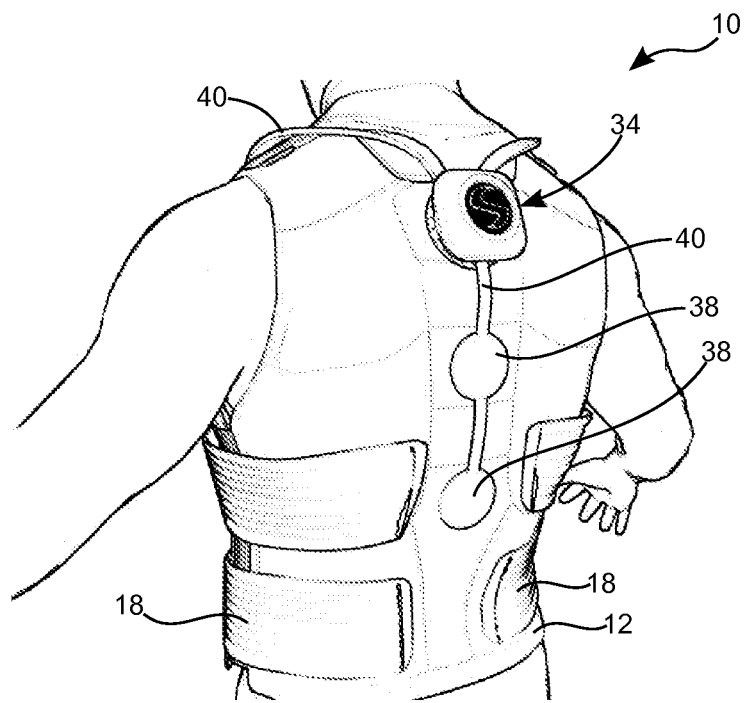
FIGS. 6A and 6B depict a rear perspective view and a front perspective view, respectively, of a cooling garment according to another embodiment of the invention.
Figure 6B:
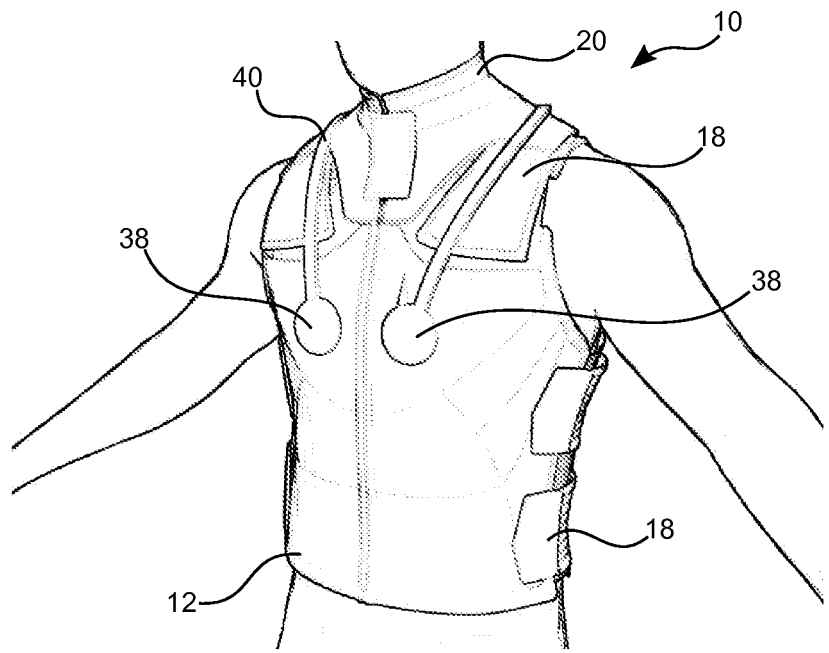

In some embodiments, as shown in FIGS. 6A-6B, the garment 10 can include additional air inlets 38 coupled to the suction device 10 by hoses 40. The air inlets 38 can be located along the front and/or the rear of the garment 10 and can extend through the garment material from the outer surface 12 to the inner surface 14 (e.g., through additional holes in the garment material). More specifically, the air inlets 38 can be open to the interior of the garment 10 to permit suction of air from the air channels 36 near each respective air inlet 38, through the air inlet 38, through the hose 40 to the suction device 34, and out the suction device 34 away from the garment 10. The additional air inlets 38 can allow air to be pulled from different areas of the garment 10 to permit more air circulation through the air channels 36.

Figure 7A:
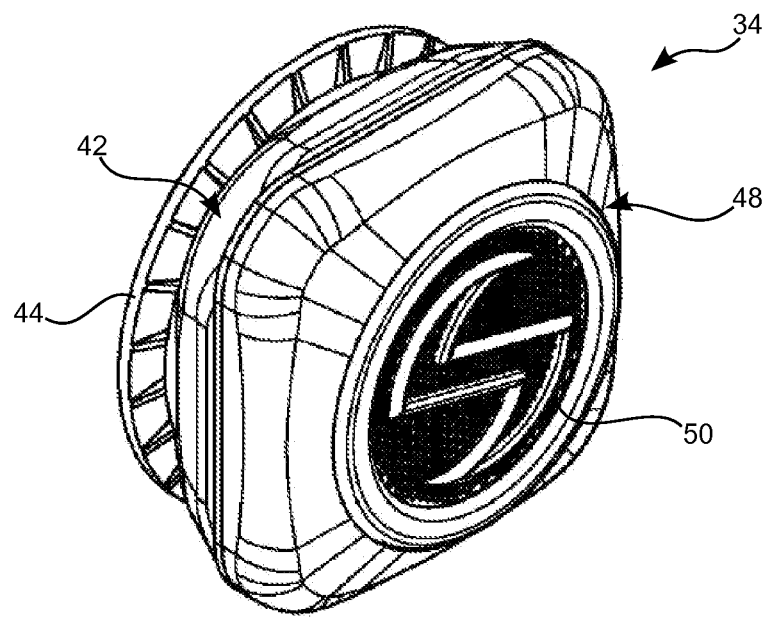
FIGS. 7A and 7B depict a front perspective view and a rear perspective view, respectively, of a suction device, according to one embodiment of the invention, for use with a cooling garment.
Figure 7B:
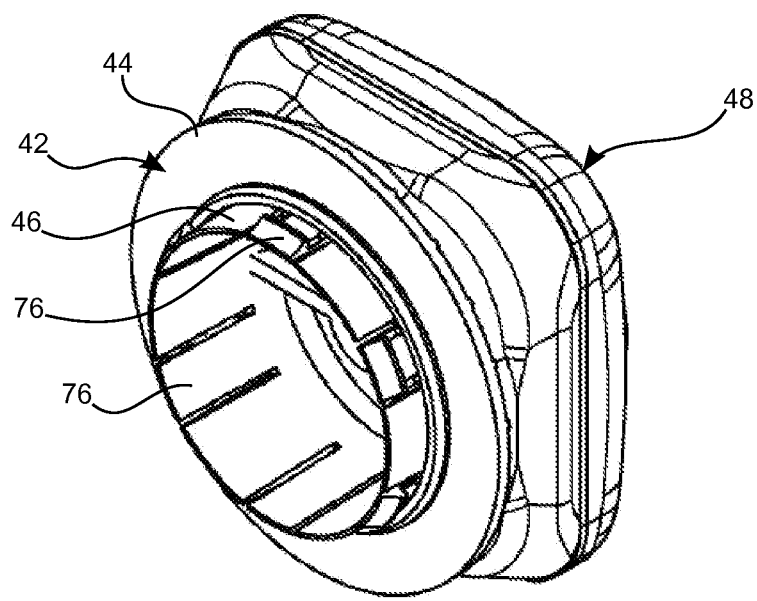
Figure 8:
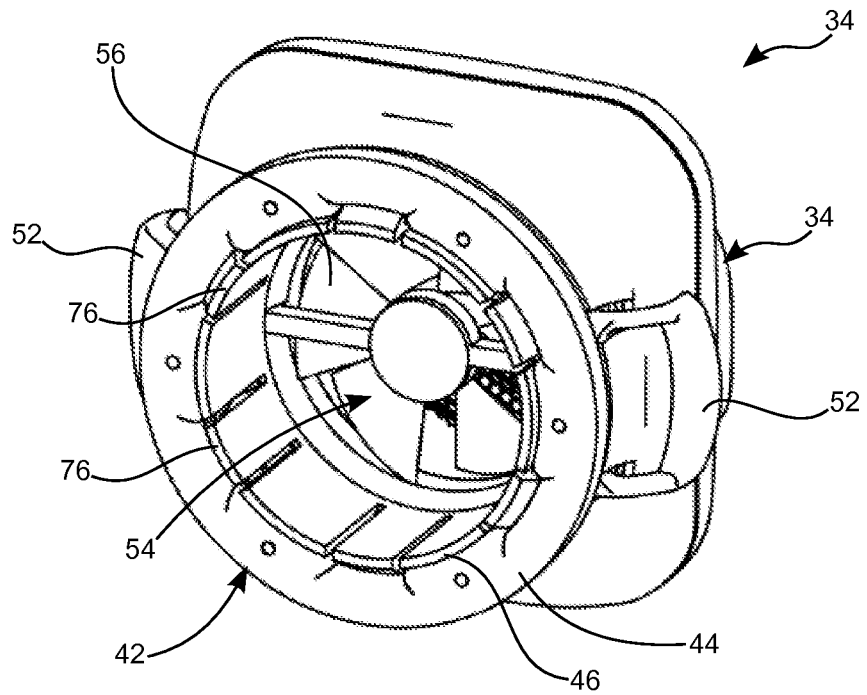
FIGS. 8 and 9 depict a rear perspective view and a front perspective view, respectively, of a suction device, according to another embodiment of the invention, for use with a cooling garment.

FIGS. 7A-10 illustrate further details of the suction device 34. As shown in FIGS. 7A and 7B, the suction device 34 can include a base 42 with an outer ring 44 and a coupling ring 46, and a cover 48 with a screen 50. The coupling ring 46 can protrude outward from the outer ring 44, as shown in FIG. 7B, or can be set substantially within the outer ring 44, as shown in FIG. 8.

Figure 9:
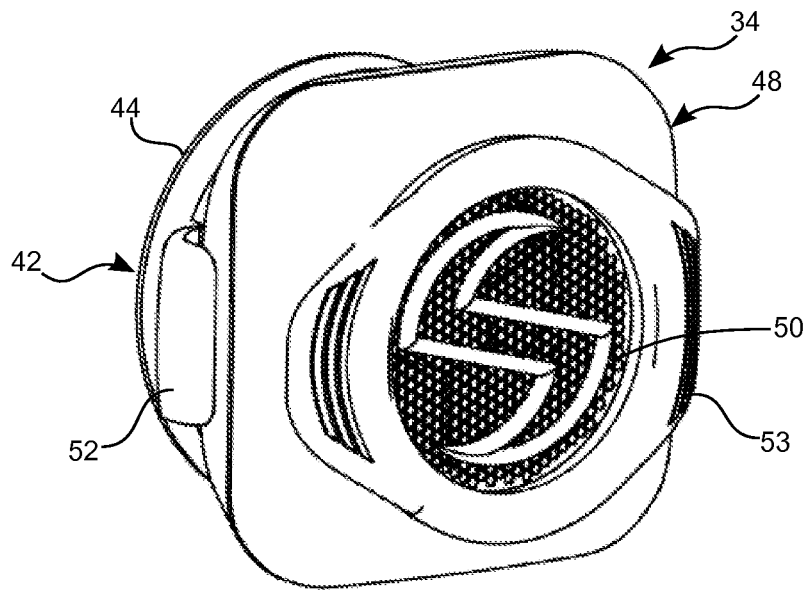

In some embodiments, as shown in FIGS. 8 and 9, the cover 50 can be detachable from the base 42 via a suitable coupling mechanism, such as one or more clips 52 on the base 42 that snap into one or more grooves (not shown) on the cover 48. In addition, in some embodiments, the screen 50 can be removable from the cover 48. For example, as shown in FIG. 9, the screen 50 can include grooves 53 to facilitate twisting off the screen 50 away from the cover 48.

Figure 10:
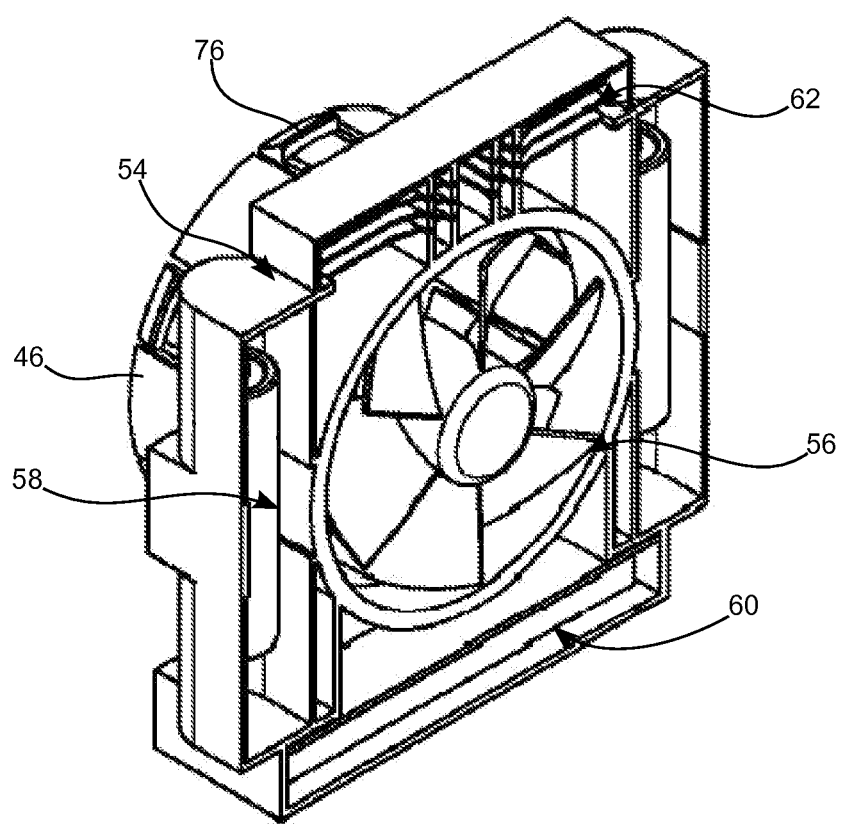
FIG. 10 depicts a perspective view of a fan mechanism, according to one embodiment of the invention, for use with a suction device.

In some embodiments, the base 42 and the cover 48 form a housing to enclose a fan mechanism 54, as shown in FIGS. 8 and 10, that provides suction force of the suction device 34. The fan mechanism 54 can include a fan 56, power storage, such as batteries 58, a controller and/or other associated electronics 60, and, optionally, a power generator 62. The controller 60 can operate the fan 56 and can be powered by the batteries 58.

Generally, the coupling ring 46 defines a suction inlet, while the screen 50 defines a suction outlet. As a result, the controller 60 can operate the fan 56 to force air in through the suction inlet (i.e., from the interior of the garment 10) and outward through the suction outlet (i.e., to the exterior of the garment 10). Suctioning air out of the garment 10, as opposed to blowing air into the garment 10, can prevent the garment 10 from billowing out, becoming uncomfortable for the user, and reducing contact between the inner surface and the user's body for heat transfer.

In some embodiments, the batteries 58 can be rechargeable via the power generator 62. The power generator 62 can be a solar power generator or a piezoelectric or kinetic generator. With a piezoelectric generator, the wearer's movement can help power the suction device 34. Additionally, the reflectors 24 can help reflect light and heat and, thus, the suction device 34 would require less energy to keep the wearer cool. Furthermore, in some embodiments, the controller 60 can operate the fan 56 based on input from an on/off switch (not shown). In other embodiments, the controller 60 can be in communication with sensors (e.g., from sensor areas 32, shown in FIG. 1A) and can operate the fan 56 based on input from the sensors. For example, the sensors can include a temperature sensor, such as a micro-thermostat, coupled to the inner surface 14 to measure the user's body temperature. The controller 60 can be programmed to turn on the fan 56 and/or adjust a speed of the fan 56 when the user's body temperature reaches a predetermined limit.

Figure 11A:
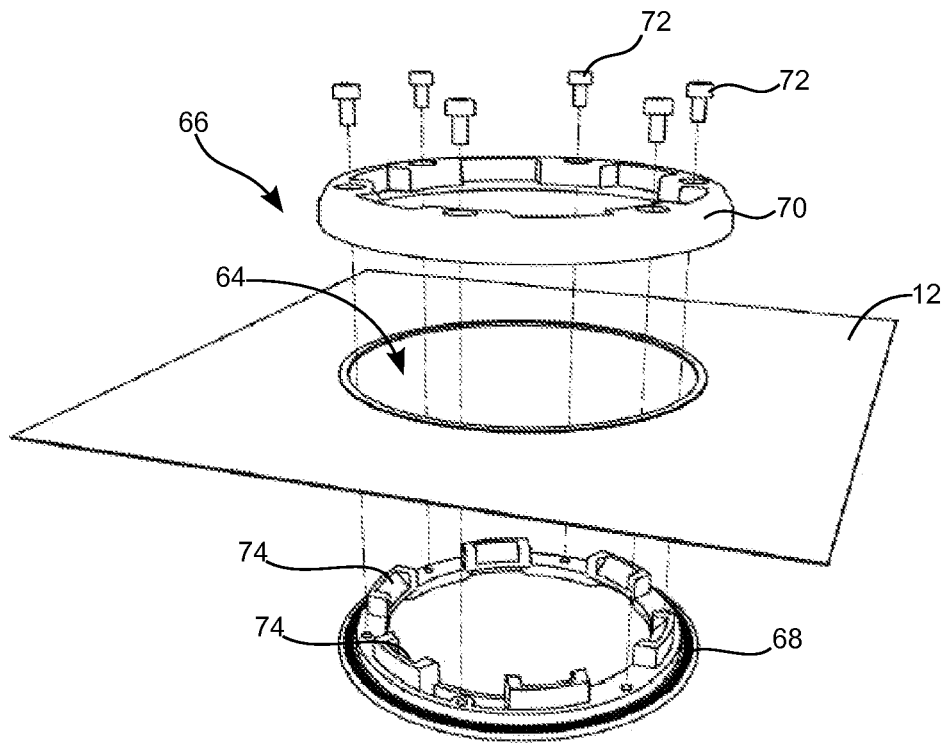
FIG. 11A depicts an exploded parts view of a fixing ring, according to one embodiment of the invention, for use with a cooling garment.
Figure 11B:
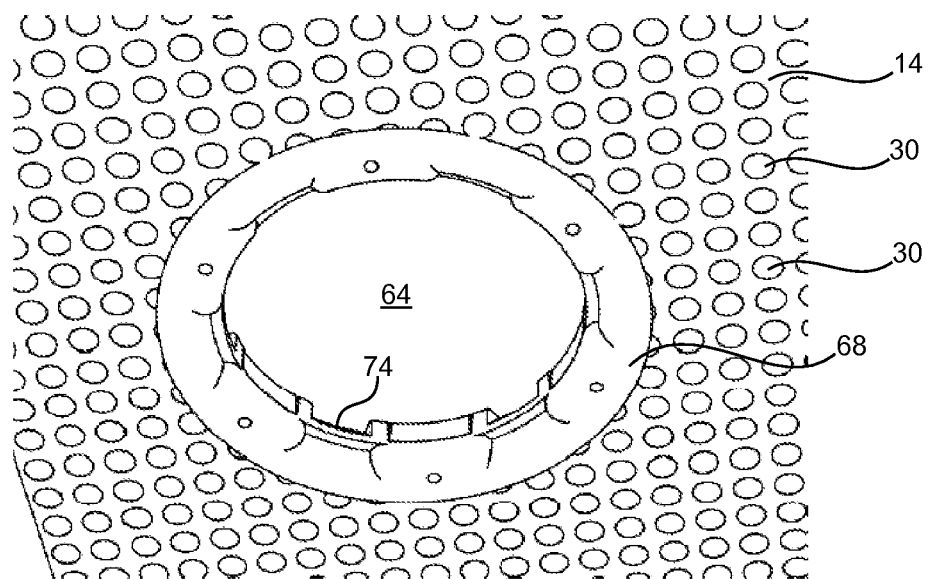
FIG. 11B depicts an underside view of the fixing ring of FIG. 11A.

In some embodiments, the suction device 34 can be permanently coupled to the garment 10. In other embodiments, the suction device 34 can be detachable from the garment 10. More specifically, as shown in FIGS. 11A-11B, the garment 10 can include a hole 64 extending through the garment 10. The garment 10 can further include a fixing ring 66 coupled to the garment material around the hole 64. The fixing ring 66 can include an internal ring 68 adjacent to the inner surface 14, an external ring 70 adjacent to the outer surface 12, and couplings, such as screws 72 that couple together the internal ring 68 and the external ring 70, as shown in FIG. 11C.

Figure 11C:
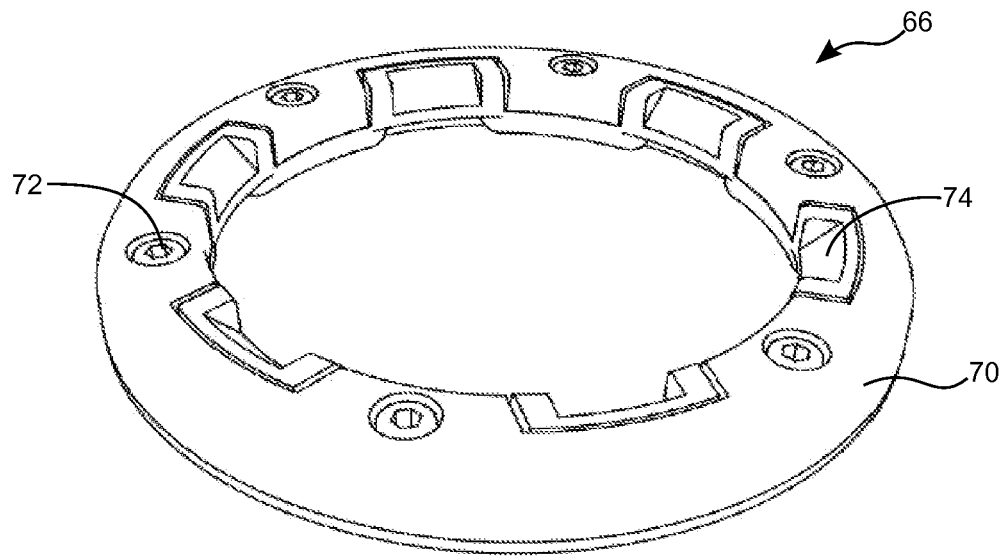
FIG. 11C depicts a perspective view of the fixing ring of FIG. 11A.
Figure 12:
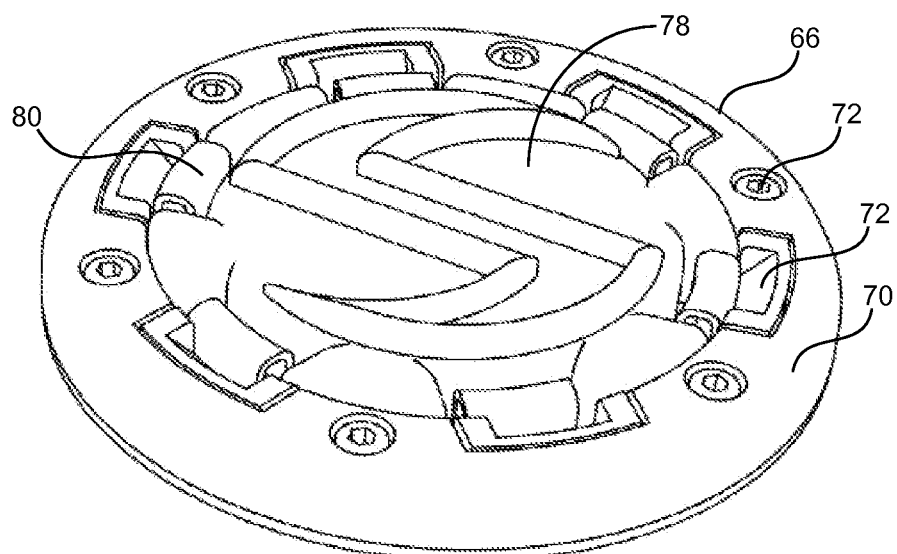
FIG. 12 depicts a perspective view of a fixing ring and a cover, according to one embodiment of the invention, for use with a cooling garment.

As shown in FIGS. 11A-11C, the fixing ring 66 can include snap fittings 74. The snap fittings 74 can be located on the internal ring 68, as shown in FIGS. 11A-11C, or, in some embodiments, on the external ring 70. The snap fittings 74 can provide a universal coupling for a variety of accessories to the garment 10, such as the suction device 34. In particular, referring back to FIG. 7B, the coupling ring 46 of the base 42 can include mating snap fittings 76. As a result, the suction device 34 can be pushed into the hole 64 until the snap fittings 74, 76 snap together in order to the couple the suction device 34 to the garment 10. Additionally, in some embodiments, as shown in FIG. 12, a cover 78 can include mating snap fittings 80. As a result, the cover 78 can be pushed into the hole 64 until the snap fittings 74, 80 snap together in order to couple the cover 78 to the garment 10.

Accordingly, the universal coupling of the fixing ring 66 allows a user to selectively wear and use the garment 10 with or without the suction device 34. For example, with the cover 78 attached, the garment 10 acts as a passive cooling garment (similar to the garment 10 of FIGS. 1-3), whereas with the suction device 34 attached, the garment 10 may be considered an active cooling garment. Furthermore, additional accessories may be coupled to the fixing ring 66. For example, different covers 78 can be interchangeable. In one example, the cover 78 may substantially comprise the same breathable material as the garment 10. In another example, the cover 78 may substantially comprise a metal or plastic material. In another example, a lid (not shown) can be configured to be coupled to both the fixing ring 66 and the coupling ring 46 of the suction device 46, thus serving as an intermediate connection between the fixing ring 66 and the coupling ring 46. The lid can be configured to receive the hoses 40 (described above with respect to FIGS. 6A-6B) so that the fan mechanism 54 can also pull air through the hoses 40. In yet another example, the cover 78 can include a plurality of sensors (not shown) configured to sense or measure one or more user variables, such as body temperature. Alternatively, the internal ring 68 may be fitted with various sensors. Such sensors can wirelessly transmit data or measurements to the controller 60 and/or a user's smartphone.

As described above, embodiments of the invention provide a cooling garment 10 configured to maintain a cooling effect for prolonged periods. The suction device 34 can be operated to facilitate evaporate cooling in addition to the conduction cooling achieved by the cooling gel chambers 26 via the protrusions 30. In addition, because the garment 10 operates a combination of active and passive cooling, the garment 10 can still provide cooling effects after the suction device 24 is turned off, unlike other active cooling systems. The suction device 34 can be compact, completely enclosed within a single housing, and strategically placed to allow the user to perform activities while wearing the garment 10, without requiring additional bulky power sources or attached cooling mechanisms. Finally, in some embodiments, the garment 10 can include bulletproof material over the outer surface 12 to facilitate military or police uses of the garment 10.

We claim:

1. A cooling upper torso garment comprising:
   a garment material configured to be worn on a user's upper body, the garment material including an outer surface, an inner surface, and a plurality of holes therethrough;
   the outer surface comprising a plurality of chambers;
   gel material within the plurality of chambers;
   protrusions extending from the inner surface, wherein the garment material is configured to compress against the user's body when worn so that the protrusions contact the user's body and define air channels between the protrusions, the inner surface, and the user's body;
   a plurality of fixing rings coupled to the garment material around each of the plurality of holes; and
   a portable suction device configured to be detachably coupled to one of the plurality of fixing rings; the portable suction device configured to circulate air through the air channels when the cooling upper torso garment is donned.

2. The cooling upper torso garment of claim 1 wherein the suction device is detachable from the fixing ring.

3. The cooling upper torso garment of claim 2 and further comprising a cover configured to be coupled to the fixing ring when the suction device is removed.

4. The cooling upper torso garment of claim 1 wherein the suction device comprises a fan mechanism including a fan, a power source, and a controller.

5. The cooling upper torso garment of claim 4 wherein the fan mechanism includes a piezoelectric power generator configured to generate power from the user's movements while wearing the cooling garment.

6. The cooling upper torso garment of claim 1 wherein the garment material is a plastic material.

7. The cooling upper torso garment of claim 1 and further comprising reflectors coupled to the outer surface and configured to reflect at least one of light and heat away from the outer surface.

8. The cooling upper torso garment of claim 1 and further comprising tightening straps coupled to the outer surface and configured to tighten the cooling garment against the user's body.

9. The cooling upper torso garment of claim 1 and further comprising an air inlet extending through the garment material from the outer surface to the inner surface and a hose coupling the air inlet to the portable suction device.

10. The cooling upper torso garment of claim 1 and further comprising a sensor configured to sense one of a temperature and a pulse of the user.

11. The cooling upper torso garment of claim 10 wherein the portable suction device comprises a fan mechanism including a fan, a power source, and a controller, and the sensor is in communication with the controller.

12. The cooling upper torso garment of claim 10 and further comprising a Bluetooth transmitter in communication with the sensor and configured to wirelessly transmit sensor information to a smartphone.

13. A cooling upper torso garment comprising:
    a garment material configured to be worn on an user's upper body, the garment material including an outer surface, an inner surface and a plurality of holes therethrough;
    the outer surface includes a plurality of chambers;
    gel material within the plurality of chambers;
    protrusions extending from the inner surface, wherein the garment material is configured to compress against the user's body when worn so that the protrusions contact the user's body;
    a plurality of fixing rings coupled to the garment material around each of the plurality of holes; and
    a portable suction device configured to be detachably coupled to one of the plurality of fixing rings;
    the portable suction device configured to circulate air through the air channels when the cooling upper garment is donned;
    the portable suction device includes a piezoelectric power generator configured to generate power thereto.

14. The cooling upper torso garment of claim 13, wherein the suction device further comprises a fan, a rechargeable battery electrically coupled to the piezoelectric power generator, and a controller electrically coupled to the battery.

15. The cooling upper torso garment of claim 14, wherein the controller is configured to selectively activate the fan.

16. The cooling upper torso garment of claim 15 and further comprising a temperature sensor coupled to the inner surface and configured to communicate with the controller, wherein the controller is configured to selectively activate the fan based on input from the temperature sensor.

17. The cooling upper torso garment of claim 13 wherein the suction device further comprises a housing enclosing the piezoelectric power generator, wherein the housing comprises a base and a removable cover.

18. The cooling agent of claim 17 wherein the plurality of fixing rings comprises snap fittings configured to receive one of the suction device and a cover.

19. The cooling upper torso garment of claim 13 and further comprising a hose coupled to the garment material and the suction device, wherein the portable suction device is configured to pull air from the air channels, through the hose, and out of the portable suction device away from the cooling garment.

* * * * *